United States Patent [19]

Van Blitterswijk et al.

[11] Patent Number: 5,811,804
[45] Date of Patent: Sep. 22, 1998

[54] ELECTRON MICROSCOPE WITH RAMAN SPECTROSCOPY

[75] Inventors: Clemens Antoni Van Blitterswijk, Hekendorp; Hendrick Klaas Koerten, Leiderdrop; Jan Greve, Oldenzaal, all of Netherlands

[73] Assignee: Biomaterials Research Group Stichting Azl, Leiden, Netherlands

[21] Appl. No.: 682,601

[22] PCT Filed: Jan. 24, 1995

[86] PCT No.: PCT/NL95/00033

§ 371 Date: Aug. 12, 1996

§ 102(e) Date: Aug. 12, 1996

[87] PCT Pub. No.: WO95/20242

PCT Pub. Date: Jul. 27, 1995

[30] Foreign Application Priority Data

Jan. 24, 1994 [NL] Netherlands .......................... 9400111

[51] Int. Cl.[6] ................................................. H01J 37/244
[52] U.S. Cl. .......................... 250/311; 250/397; 250/310
[58] Field of Search ................................... 250/306, 310, 250/311, 397

[56] References Cited

U.S. PATENT DOCUMENTS

| | | | |
|---|---|---|---|
| 3,624,393 | 11/1971 | Torquebiau | 250/311 |
| 4,407,008 | 9/1983 | Schmidt et al. | 358/93 |
| 4,537,477 | 8/1985 | Takagi et al. | 250/310 |
| 4,917,462 | 4/1990 | Lewis et al. | 350/319 |
| 4,929,041 | 5/1990 | Vahala et al. | 250/311 |
| 5,218,195 | 6/1993 | Hakamata | 250/216 |
| 5,272,330 | 12/1993 | Betzig et al. | 250/216 |
| 5,362,964 | 11/1994 | Knowles et al. | 250/310 |
| 5,412,211 | 5/1995 | Knowles | 250/310 |
| 5,473,157 | 12/1995 | Grober et al. | 250/306 |

FOREIGN PATENT DOCUMENTS 2 596 863  10/1987  France .
WO 92/22805  12/1992  WIPO .

*Primary Examiner*—Bruce Anderson
*Attorney, Agent, or Firm*—Young & Thompson

[57] ABSTRACT

Electron microscope provided, in the direction of the longitudinal axis, with at least one electron beam generation system, a condenser and objective lens system, a specimen chamber with a specimen mount, a projection lens system with imaging screen for the purpose of transmission electron microscopy (TEM) and/or an electron detector for the purpose of scanning electron microscopy (SEM). The microscope is used in combination with an externally positioned Raman spectrometer and an associated light source for injecting and extracting, via a window in the microscope wall, a light beam to be directed at the specimen, and specimen-related Raman radiation, respectively. In the specimen chamber, a light beam and Raman radiation guide system is provided with an optical guide to guide the light beam to—and the Raman radiation from—the specimen. The guide system and the specimen mount are displaceable with respect to one another for mutual alignment of the specimen and the optical axis of the Raman spectrometer.

7 Claims, 6 Drawing Sheets fig-1 fig-2 fig-3 fig-4 fig-7 fig-9 fig-8 fig-10

ELECTRON MICROSCOPE WITH RAMAN SPECTROSCOPY

FIELD OF THE INVENTION

The invention relates to an electron microscope provided, in the direction of the longitudinal axis, with at least one electron beam generation system, a condenser and objective lens system, a specimen chamber with a specimen mount, a projection lens system with an imaging screen for the purpose of transmission electron microscopy (TEM) and/or an electron detector for the purpose of scanning electron microscopy (SEM), for use in combination with an externally positioned Raman spectrometer and an associated light source for injecting and extracting, via a window in the microscope wall, a light beam to be directed at the specimen, and specimen-related Raman radiation, respectively. Such a microscope is disclosed by the French Patent Application FR-A-2596863.

BACKGROUND OF THE INVENTION

The electron microscope generally known from the prior art is an instrument by means of which it is possible for structures in thin specimens or surfaces to be rendered visible, for example by means of TEM, or for structures in bulk specimens to be rendered visible, for example by means of SEM, with high resolving power, in the order of magnitude of a few tenths of nanometres in the former case or of a few nanometres in the latter case.

Figure 1:
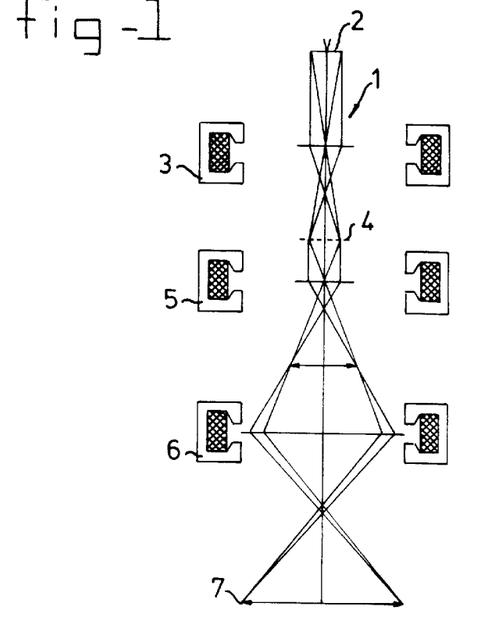
FIG. 1 shows a schematic diagram of a known transmission electron microscope (TEM)

In such a microscope, as depicted in FIG. 1, an electron beam 1 is produced in an electron gun 2 consisting of cathode, Wehnelt cylinder and anode. With the aid of a magnetic lens system 3, a so-called condenser lens system, the electron beam is focused into a coherent spot above the specimen 4, which spot may be subjected to a scanning notion.

In the case of the transmission electron microscope (TEM) the beam passes through the specimen 4 and is projected with the aid of a magnetic lens system, such as objective 5 and projection lenses 6, onto an imaging screen 7 such as a fluorescent screen. Upon incidence of the electron beam, this screen lights up and produces a magnified image of the specimen. The presence, in the specimen, of elements having varying atomic numbers results in contrast being achieved, heavy elements having a high atomic number affecting the electron trajectory in a different way than do light elements having a lower atomic number. The result of this is that, at positions where heavy elements are present, the electrons are reflected in their entirety or in part, while electrons can pass through fairly easily at positions where light elements are present. Consequently, a specimen composed of different chemical elements will therefore also transmit varying quantities of electrons. On the screen an image is formed which gives the highest brightness for positions where light elements having lower atomic numbers are present in the specimen, and the lowest brightness at positions where elements having a high atomic number are present. A sort of shadow image is thus formed.

Figure 2:
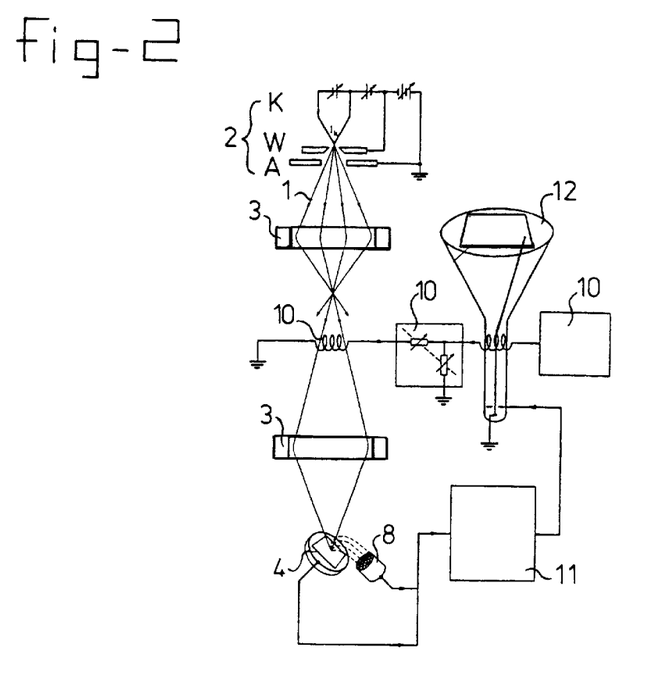
FIG. 2 shows a schematic diagram of a known scanning electron microscope (SEM)

In the case of the scanning electron microscope (SEM) which is depicted in FIG. 2 and which is essentially of the same construction as the transmission electron microscope, the electron beam 1 generated by an electron gun 2 also passes through a condenser lens system 3. The electron beam, in the case of the SEM, is focused onto a spot on the specimen, said spot being subjected to a scanning motion by means of a deflection unit 10. The electrons reflected or backscattered by the specimen 4 are intercepted at an electron detector 8 and, after amplification in 11, are used to effect intensity variations on the screen of a cathode ray tube 12 synchronized with the electron beam scanning.

The TEM provides images of thin specimen cuts and can therefore render visible the interior of specimens to be studied. In contrast, the SEM provides an image with the aid of the electrons returning from the specimen and is therefore specifically suitable for presenting images of the surface, or directly below it, of a specimen. If the specimen to be studied is a section through an object, the SEM will naturally also provide information on the interior. It is also possible, in the SEM, for the reflected electrons to be detected selectively. Thus we can distinguish between secondary electrons and backscattered electrons. The number of electrons which is detected as backscattered may be a measure for the chemical elements which are present in the specimen. Thus an element having a high atomic number will reflect more electrons than an element having a low atomic number, a difference in brightness thus being produced, which is representative for the elemental composition of the specimen.

Another possibility to obtain elemental information with the aid of the electron microscope is the use of Electron Energy Loss Spectrometry (EELS). This technique is used in transmission electron microscopy and is based on the principle that electrons are slowed down in the specimen and that the degree of slowing down depends on the density (elemental composition) of the specimen. As a result of use being made of a type of electron prism, the electrons, after having been slowed down by the specimen are deflected differently causing so-called element-specific images to be formed.

For that matter, there are also so-called scanning-transmission electron microscopes (STEM), in which the TEM and the SEM systems are combined and their imaging options are connected. In this case it will be possible, via two separate monitors, to observe both the TEM image and the SEM image.

Each of the abovementioned electron microscopes may in addition incorporate an X-ray detector. By making use of the X-rays which are released as a result of the beam-specimen interaction, it is possible, by means of this detector, to obtain information concerning the presence in the specimen of certain chemical elements. As is known, incident primary electrons from the electron beam may collide with the electrons, present in the specimen, of atoms. As a result of this collision, the electrons which are located in one of the innermost shells of the atoms making up the specimen, may be knocked out of their orbit, thus producing an unstable atom. To eliminate this instability, an electron from a high orbit having a particular energy level can drop back to said low orbit, energy being released in the process which in part is emitted in the form of X-radiation and is specific for the element in question.

Figure 3:
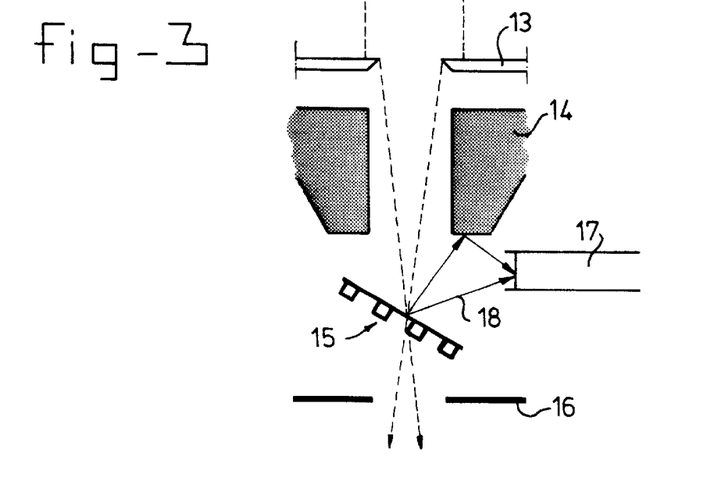
FIG. 3 shows a detail rendition of a specimen chamber with an X-ray microanalysis detector.
Figure 4:
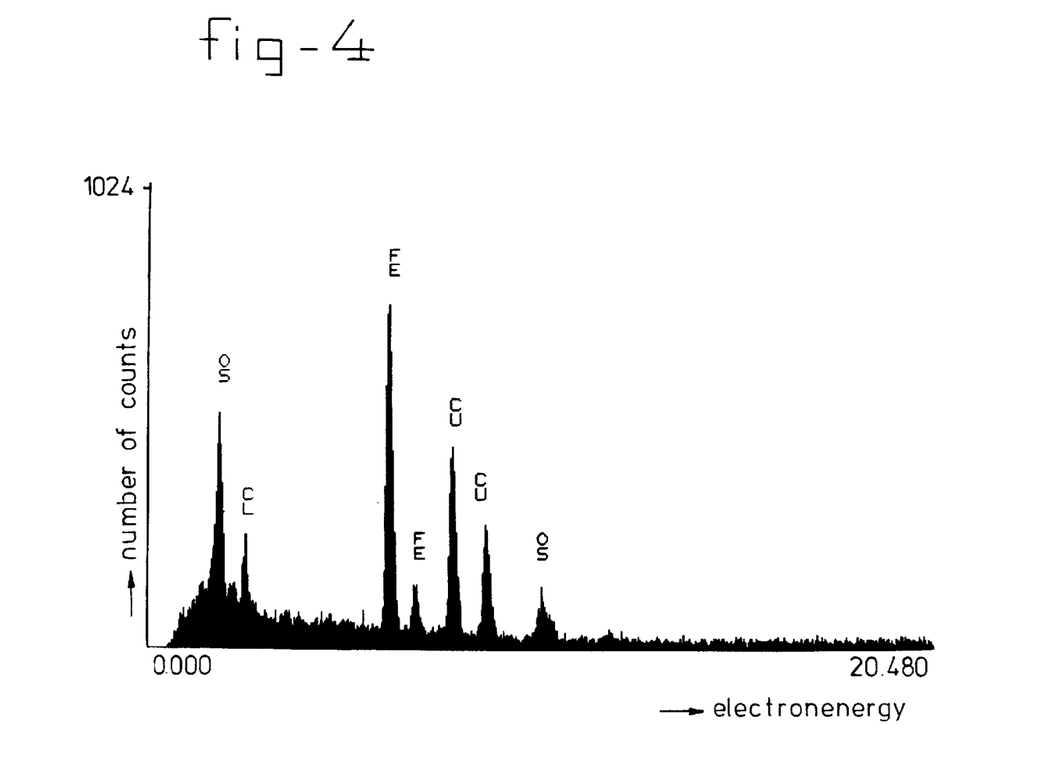
FIG. 4 shows an example of an X-ray microanalysis spectrum of an image point.

FIG. 3 indicates how the electron beam 1, after passing through the condenser aperture 13 and the pole pieces 14 impinges on the specimen placed on a grid holder 15. Part of the electron beam passes through the specimen and an objective lens 16. The X-radiation 18 released from the specimen is intercepted above the specimen in an X-ray detector 17 and can, when an image point is being investigated, be represented in the form of a spectrum on a monitor (see FIG. 4) or can, when an entire picture element is being studied, be represented in the form of an element distribution picture on another monitor.

By focusing, as stated earlier, the electron beam into a scanning spot on that part of the specimen which is to be studied, it is possible to generate the X-radiation for that specific part of the specimen. The resolving power of said X-ray microscopy is determined by the diameter of the electron beam and is in the order of magnitude of from 0.05 to 0.5 μm. The spectra obtained with the aid of said X-ray microanalysis mainly provide information on the presence of chemical elements in the specimen, but do not provide information on the structure of molecules and/or crystals in situ. It is indeed possible, with the TEM, to obtain information with respect to the occurrence of specific crystals, from the diffraction pattern which can be produced with a TEM. With a SEM, however, a diffraction pattern cannot be obtained, and the knowledge the investigator in question has of the specimen will determine whether he is able to derive, to some extent, the molecular and crystal structure from the elemental composition.

From a different optical spectroscopic technique, then, Raman spectroscopy is known, which involves irradiating a specimen with monochromatic light. The light scattered by the specimen will, in addition to light of the same wavelength as the incident light, also contain light of other wavelengths. This wavelength shift is caused by an interaction between molecules of the specimen and photons of the incident light, which results in the molecules, after interaction, remaining in a vibrational energy state which is different from the initial one. Different molecular vibrations lead to different discrete wavelength shifts. Thus information is obtained with respect to the molecular composition and molecular structure of the specimen.

Figure 5:
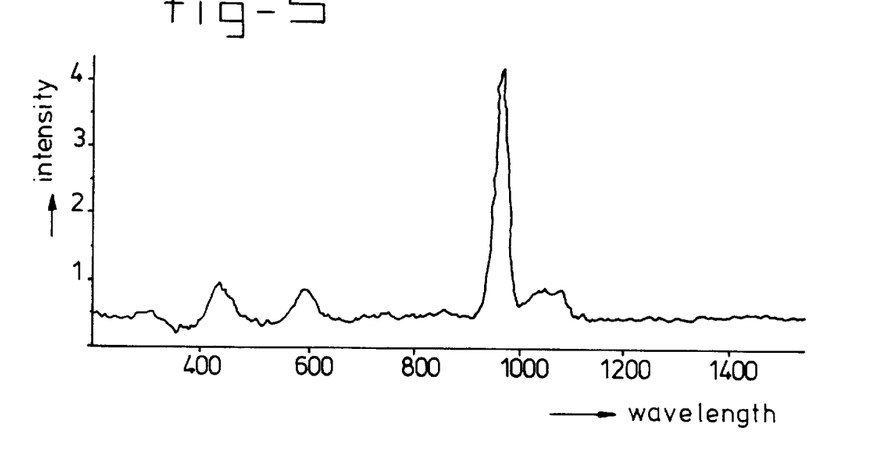
FIG. 5 shows an example of a Raman spectrum of an image point.

A Raman microspectrometer consists of an optical microscope, optically coupled to a spectrometer provided with a sensitive optical detector (photomultiplier, cooled CCD camera). The spatial resolution which can be achieved with such an instrument is determined by the optical diffraction limit (i.e. ~λ/2). The Raman photon energy collected in the optical detector may serve to form a spectrum as depicted in FIG. 5, when an image point is studied, or to display a distribution picture when an entire image element is studied.

Figure 6:
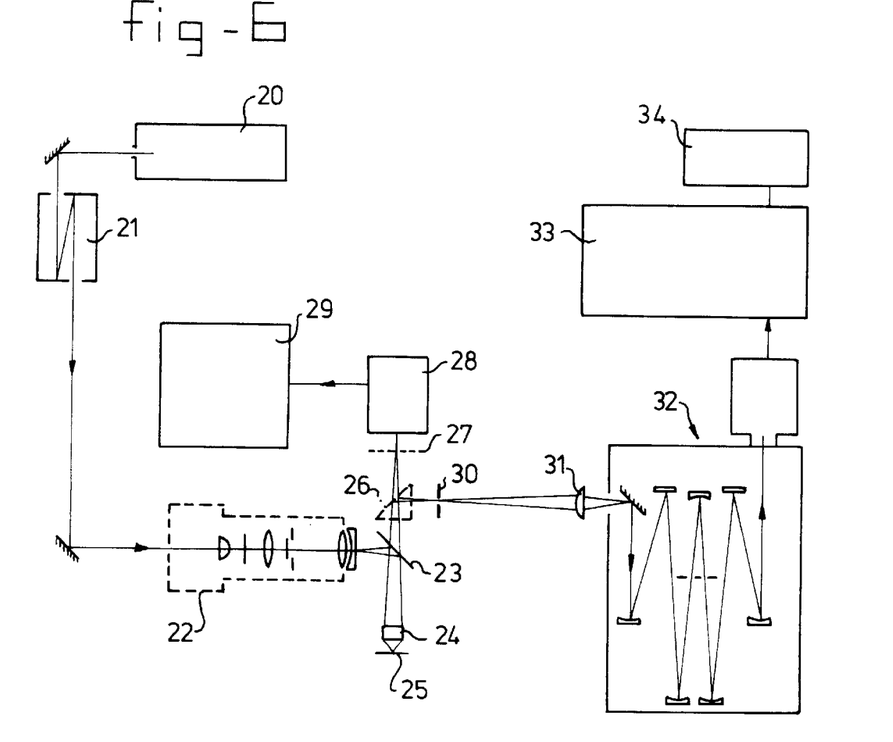
FIG. 6 shows a schematic diagram of a known Raman spectroscope.

FIG. 6 depicts a highly schematic design of a Raman spectroscope, which is used to carry out the abovementioned spectrometry. 20 indicates a light source such as a laser, 21 a laser premonochromator, 22 a lens and condenser system, 23 a beam splitter, 24 an objective, 25 a specimen, 26 a prism, 27 an ND filter, 28 a camera, 29 a monitor, 30 a spatial filter, 31 a lens, 32 a Raman spectrometer, for example a photomultiplier, 33 a control unit and 34 an x-y plotter. This Raman spectroscope can be operated in two modes when the specimen 25 is studied. In the one, or imaging mode, it is possible to present on the monitor 29, via the camera, a distribution picture of the information from the specimen in the spectrum for specific Raman components. In the other, or analysis mode, a Raman spectrum of small areas or image points of the specimen can be studied by means of the spectrometer 32.

A drawback of said known Raman spectroscopy is the relatively wide wavelength spectrum and the large spot size of the light beam with which the specimen could be irradiated. As a result of the use of microlaser techniques, the resolving power of Raman spectrometry has now been greatly improved. In addition, work is currently being done on the development of Raman spectrometry in combination with Scanning Near Field Microscopy (SNOM). In this application the light required to generate the Raman signal is radiated in via a nanotip of a hollow tube or fibre whose terminal piece has a smaller cross section than the wavelength of the light used. As a result, the specimen is "illuminated" by an extremely thin light beam which provides for a resolving power which is below the theoretical value of the resolving power of a normal optical microscope.

The abovementioned electron microscopy and Raman spectroscopy are generally carried out separate from one another. If the information from these two techniques has to be related, it is extraordinarily difficult to synchronize the results of these techniques. In the meantime there is a great need, both in material science and in medical-biological research, for identifying molecules and crystals in electron microscopic specimens.

The abovementioned French patent application discloses the use of an electron microscope in combination with an externally positioned Raman spectrometer and associated light source. The light beam of the light source is injected into the microscope via a window in the microscope wall at the level of the condenser and objective lens system and is reflected directly at 45°, via a reflection plate positioned on the longitudinal axis of the electron microscope, in the direction along the longitudinal axis of the electron microscope, and is directed at the specimen. The Raman radiation subsequently emanating from the specimen is deflected via the same reflection plate and is extracted, via the window, towards the Raman spectrometer. In practice it proved most difficult thus to achieve alternating or virtually simultaneous operation of electron microscopy and Raman spectrometry. The combination of a light-optical system and an electron-optical system, simultaneously present in the space above the specimen compartment around the electron longitudinal axis, quite quickly causes deformation of the electron beam, for example astigmatism. Furthermore, the space between the pole shoes and the specimen is limited, to the extent that the introduction of the light-optical system is disadvantageous, in particular in the case of transmission electron microscopy. This limited space also presents problems in positioning the X-ray analysis detector.

SUMMARY OF THE INVENTION

The object of the invention is to overcome the abovementioned problems and to further develop an electron microscope in such a way that an electron microscope is obtained which is easy to handle and is efficiently combined with Raman spectrometry, in which electron microscope the results of the two analysis techniques are coordinated effectively.

This is achieved, according to the invention, in an electron microscope of the type mentioned in the preamble, in that, in the specimen chamber, a light beam and Raman radiation guide system is provided to guide the light beam to—and the Raman radiation from—the specimen, and in that the guide system and the specimen mount are displaceable with respect to one another for mutual alignment of the specimen and the optical axis of the Raman spectrometer.

With this embodiment according to the invention it was found, surprisingly, that as a result of making use of modern techniques in generating light beams of very small diameter and high intensity the use of Raman spectroscopy in terms of resolving power is highly expedient in electron microscopy.

BRIEF DESCRIPTION OF THE DRAWINGS

The invention will be explained in more detail by means of a specific embodiment with reference to the drawings, in which.

DETAILED DESCRIPTION OF THE INVENTION

Figure 7:
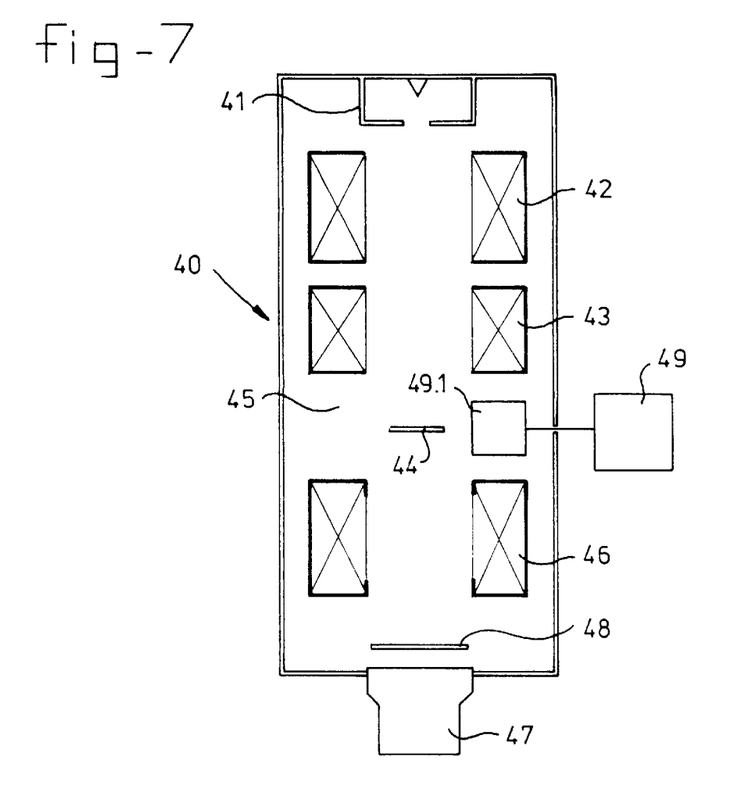
FIG. 7 shows, by way of a sketch, a schematic diagram of a specific embodiment according to the invention in a transmission electron microscope.

In FIG. 7, 40 schematically indicates a transmission electron microscope. In this electron microscope, 41 indicates an electron gun, 42 a condenser lens system, 43 an objective lens, 45 generally a specimen chamber, 44 a specimen mount, 46 an intermediate and projection lens system, 48 an imaging screen, 47 a CCD camera, and 49 and 49.1 in combination a Raman microanalysis system with injection and extraction mechanism.

Figure 8:
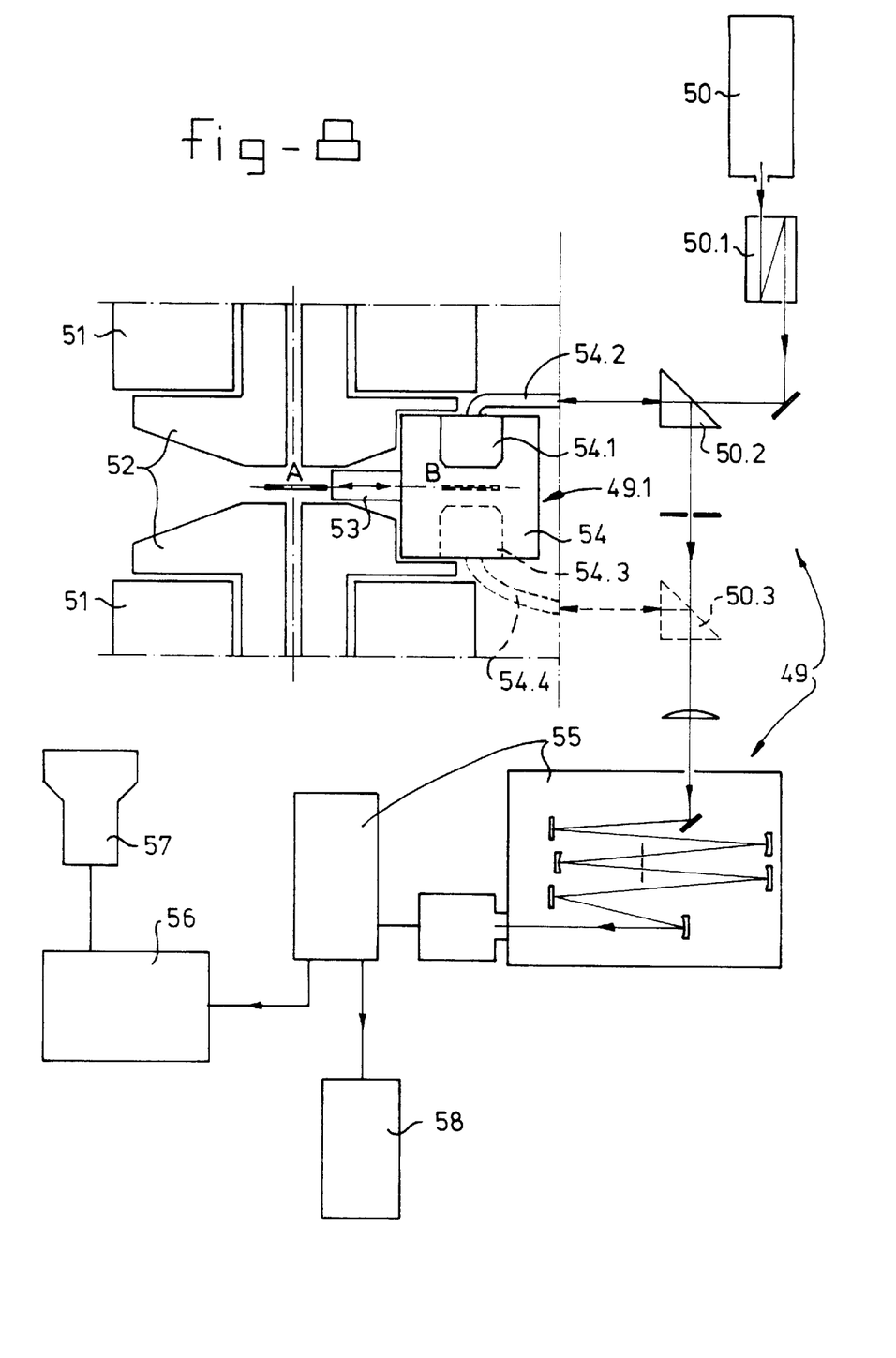
FIG. 8 shows a more detailed elaboration of the specific embodiment from FIG. 7.

FIG. 8 depicts the combination of components 49 and 49.1 from FIG. 7 in detail, 50 indicating a light source such as a microlaser, 50.1 a premonochromator, 50.2 a semitransparent prism, 51 in general a lens system, 52 pole shoes, 53 a specimen displacement mechanism, 54 a light beam and Raman radiation guide system provided with an objective and lens system 54.1 and an optical guide 54.2, for guiding and injecting the light beam towards the specimen and for guiding and extracting the Raman signals emanating from the specimen, and 55 a Raman microspectrometer. The light beam and Raman radiation guide system 54 can additionally be provided with a second objective and lens system 54.3 and a light guide 54.4 for guiding and extracting the Raman signals emanating from the specimen to the additionally provided semi-transparent prism 50.3.

This system can be combined with an x-y plotter 58 and/or with a computer 56 which contains an image memory, so that the electron-microscopic image can be read in with the aid of a CCD camera 57. Subsequently, a cursor in this image may serve to allow the user to orient himself and to guide and indicate the positioning of the specimen in the optical longitudinal axis of the Raman microspectroscope.

Figure 9:
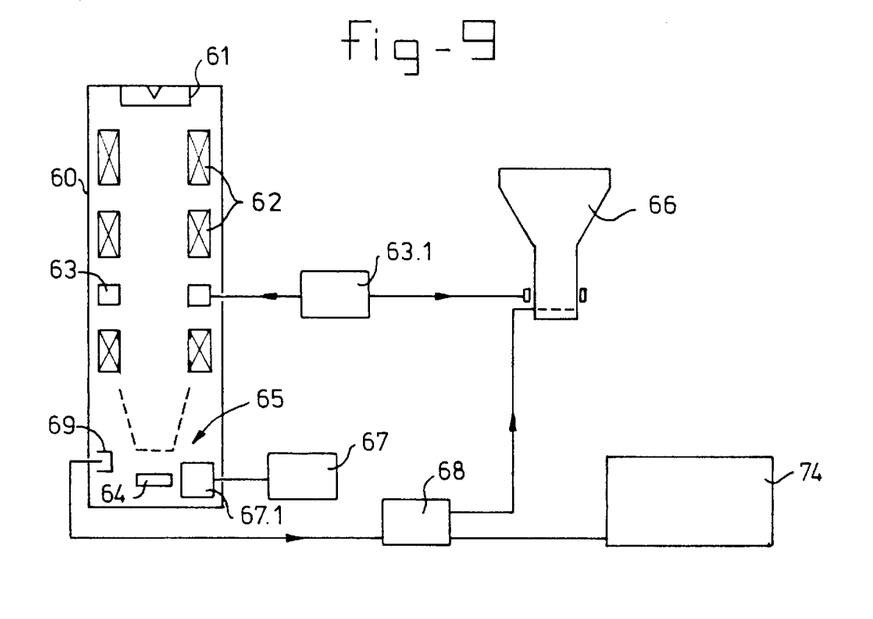
FIG. 9 shows, by way of a sketch, a schematic diagram of another specific embodiment according to the invention in a scanning electron microscope.

In FIG. 9, which shows an example of an embodiment in the scanning electron microscope, 60 schematically indicates a scanning electron microscope. In this electron microscope, 61 indicates an electron gun, 62 a condenser lens system, 63 a beam deflector controlled by a scanning generator 63.1, 65 in general a specimen chamber, 64 a specimen mount, 69 an electron or X-ray detector, 68 an amplifier, 66 an imaging screen, 74 an image computer, 67 and 67.1 in combination a Raman microanalysis system with injection and extraction mechanism.

Figure 10:
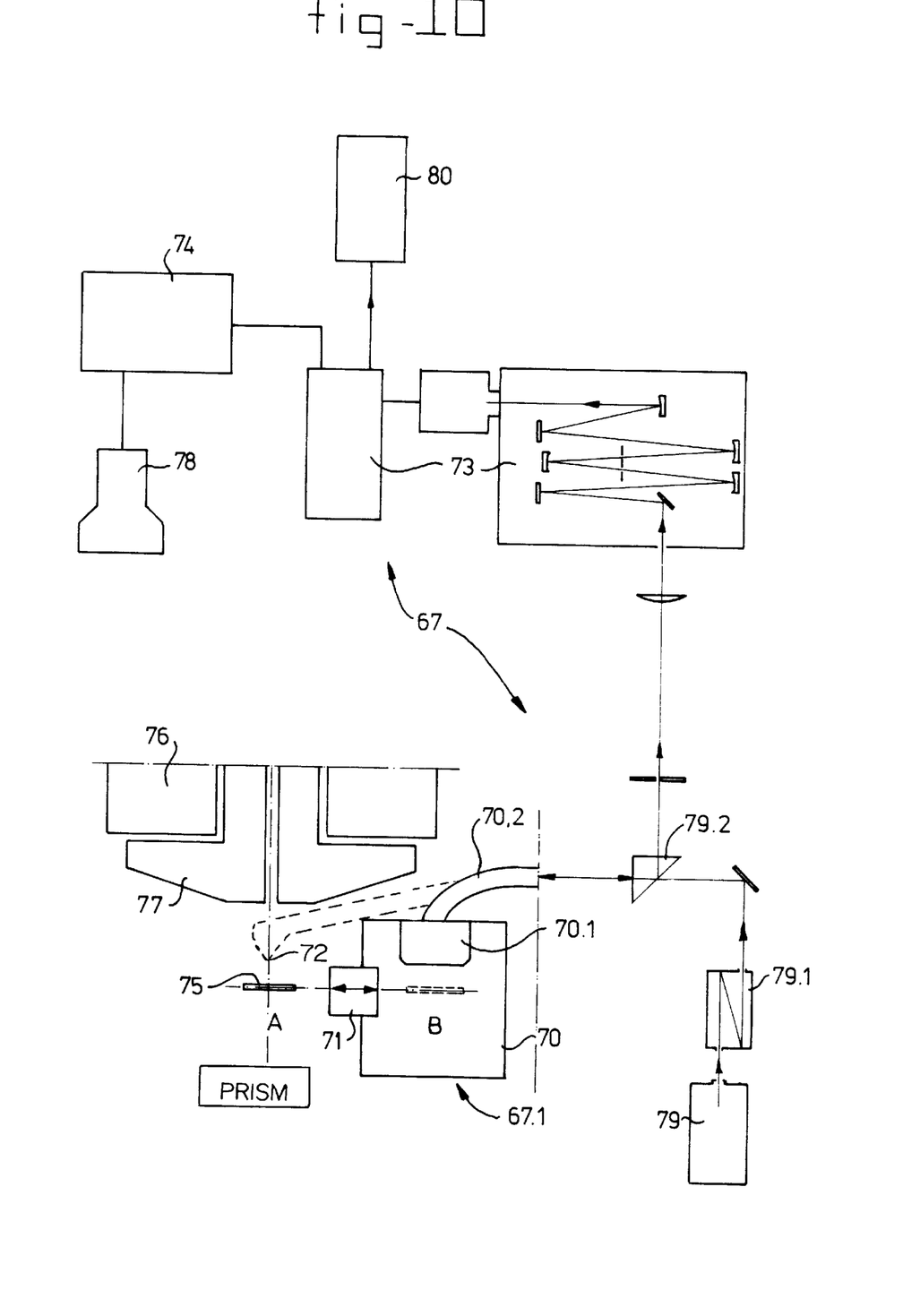
FIG. 10 shows a more detailed elaboration of the specific embodiment from FIG. 9.

FIG. 10 depicts the combination of components 67 and 67.1 from FIG. 9 in detail, 79 indicating a light source such as a microlaser, 79.1 a premonochromator, 79.2 a semitransparent prism, 70 in general an objective and lens system, 71 a specimen displacement mechanism, 76 in general a lens system, 75 a specimen, 77 pole shoes, 70 a light beam and Raman radiation guide system provided with an objective and lens system 70.1 and an optical guide 70.2, for guiding and injecting the laser light towards the specimen 75 and for guiding and extracting the Raman signals emanating from the specimen, and 73 a Raman microspectrometer. This system can be combined with an x-y plotter 80 and/or with a computer 74 which contains an image memory, so that the electron-microscopic image can be read in with the aid of a CCD camera 78. Subsequently, a cursor in this image may serve to allow the user to orient himself and to guide and indicate the positioning of the specimen in the optical longitudinal axis of the Raman microspectroscope.

It goes without saying that, although this is not indicated, it is possible for both types of microscopes indicated in the FIGS. 8 and 10 to be fitted with a microlaser and Raman signal detector of the Raman spectroscope embodied inside the microscope per se, and/or to be fitted with an X-ray microanalysis detector, as in FIG. 3.

In the abovementioned specific embodiments in FIGS. 8 and 10, the laser and Raman guide system has been positioned next to the microscope axis in an adjustable manner, it being possible for the specimen to be separately aligned therewith. In both examples, the specimen mount 53 or 71 is movable, in a controllable manner from the outside, between the positions A and B, which makes it possible for measurements with the electron detector (and X-ray detector) in position A to be carried out alternately with measurements with the Raman spectroscope in position B. In the latter position, the laser beam is injected via the optical guide or fibre and is radiated in, parallel to the longitudinal axis of the microscope, onto the specimen, the Raman radiation emanating from the specimen being extracted. With the design according to the invention in a transmission electron microscope according to FIG. 8 it is also possible, when studying thin specimens, for the Raman radiation emerging at the underside of the specimen to be collected and extracted via the lens 54.3 and the optical guide 54.4.

In both the abovementioned specific embodiments from the FIGS. 8 and 10 it is also possible, instead of displacing the specimen between the positions A and B, for the light beam and Raman radiation guide system 54 or 70 to be displaced, owing to the flexible connection with the light guide, to the position A directly above the specimen. The specimen is then irradiated by the light beam from the space directly below the pole shoes 52 or 77.

It is further possible, when near field microscopy with a nanotip 72 at the end of the light guide is used, rather than displacing the specimen between the positions A and B, to displace the flexible light guide 54.2 or 70.2 to the position A directly above the specimen. With this design, having a nanotip 72 at the light guide, an objective and lens system 54.1 or 70.1 is unnecessary.

The light beams which can be generated with modern microlasers can have a high intensity with a very narrow bandwidth. At the same time, because the cross-section of the laser beam can be made small. Raman microspectroscopy consequently, in terms of resolving power, will approach X-ray microanalysis. Use of the SNOM in combination with the Raman microspectrometer even permits a resolving power which is below the theoretically achievable resolving power of an optical microscope.

The invention can advantageously be applied both in material science and in biology. With, for example, the manufacture of implants for bone tissue it is important to characterize the apatite crystals present in the inorganic matrix of bone tissue, and the crystals in calcium phosphate ceramics which are used as bone implants. In addition it is important to establish, in laboratory animal experiments, whether, and if so, to what extent, changes in the composition of the two matrices occur during the implantation period. Likewise, it is then advantageous to establish the type of possible degradation products produced by cellular disintegration.

With the aid of the abovementioned design according to the invention it is possible, to considerable advantage, for (portions of) a specimen to be studied accurately by simultaneous observation of the electron microscopy picture on a first monitor and the Raman spectrum/spectroscopy picture on a second monitor, supplemented, if required, by the X-ray analysis spectrum/X-ray analysis picture on a third monitor. Since the X-ray analysis provides elemental information, and Raman analysis provides molecular information, the two can be combined in a surprising manner, which makes it possible for both the X-ray signal and the Raman signal separately to be interpreted more effectively, the two enhancing one another.

Given the specific embodiments indicated above, the number of applications to be expected for molecular-identification systems in an electron microscope is extraordinarily large.

We claim:

1. In an electron microscope (40; 60) provided, in the direction of a longitudinal axis, with at least one electron beam generation system (41; 61), a condenser and objective lens system comprising a plurality of elements (42, 43; 62, 62), a specimen chamber (45; 65) with a specimen mount (44; 64), a projection lens system (46) with imaging screen (48) for the purpose of transmission electron microscopy (TEM) and/or an electron detector (69) for the purpose of scanning electron microscopy (SEM), for use in combination with an externally positioned light source (50; 79) and associated Raman spectrometer (55; 73) with a light beam and Raman radiation guide system for injecting, via a window in a microscope wall, a light beam to be directed at the specimen respectively for extracting via said window of specimen-related Raman radiation, the improvement wherein the light beam and Raman radiation guide system (49.1; 67.1) is provided within the specimen chamber (45; 65) aside from the microscope longitudinal axis, and a specimen (53; 71) displacement mechanism is fitted to displace the specimen mount (44; 64) from a position in the longitudinal axis of the microscope transversely to a position aside from said longitudinal axis in which the optical axis in said guide system (49.1; 67.1) and the specimen are aligned.

2. Electron microscope according to claim 1, wherein the light beam and Raman radiation guide system comprises an optical guide (54.2; 70.2) connected to the externally positioned light source (50; 79) and associated Raman spectrometer (55; 73).

3. Electron microscope according to claim 2, wherein the light beam and Raman radiation guide system (49.1; 67.1) further comprises an objective and lens system (54.1: 70.1) positioned at the end of the optical guide (54.2; 70.2).

4. Electron microscope according to claim 2, wherein the optical guide is extended such that its end is displaceable to a position in which the optical axis running out from the end of the guide coincides with the longitudinal axis of the microscope and is aligned with the specimen.

5. Electron microscope according to claim 4, wherein the optical guide is embodied with a nanotip at its end, for the purpose of near field microscopy.

6. Electron microscope according to claim 1, wherein an X-ray analysis detector is fitted in the specimen chamber, to record X-rays generated in the specimen, for the purpose of X-ray analysis.

7. Electron microscope according to claim 1, wherein an electron prism is fitted, beyond the specimen in the direction of the longitudinal axis, for the purpose of electron energy loss spectrometry.

\* \* \* \* \*